US007542795B2

(12) United States Patent
Brodnick

(10) Patent No.: US 7,542,795 B2
(45) Date of Patent: Jun. 2, 2009

(54) VECTOR SUPERIMPOSITION AND GRAPHICAL DISPLAY OF PHYSIOLOGICAL DATA WITHOUT OR BEFORE ANALYSIS

(75) Inventor: Donald E. Brodnick, Cedarburg, WI (US)

(73) Assignee: The General Electric Company, Schenectady, NY (US)

( * ) Notice: Subject to any disclaimer, the term of this patent is extended or adjusted under 35 U.S.C. 154(b) by 554 days.

(21) Appl. No.: 11/194,724

(22) Filed: Aug. 1, 2005

(65) Prior Publication Data

US 2007/0027398 A1 Feb. 1, 2007

(51) Int. Cl.
*A61B 5/04* (2006.01)
(52) U.S. Cl. .................. 600/512; 600/509; 600/523
(58) Field of Classification Search .......... 600/509, 600/512, 523
See application file for complete search history.

(56) References Cited

U.S. PATENT DOCUMENTS

| 3,548,813 | A | 12/1970 | Berner | 128/2.06 |
|---|---|---|---|---|
| 3,654,916 | A | 4/1972 | Neilson | 128/2.06 |
| 4,106,495 | A | 8/1978 | Kennedy | 128/2.06 |
| 4,136,690 | A | 1/1979 | Anderson et al. | 128/2.06 |
| 4,175,337 | A | 11/1979 | Benjo | 35/17 |
| 4,697,597 | A | 10/1987 | Sanz et al. | 128/699 |
| 5,474,079 | A * | 12/1995 | Brodnick et al. | 600/524 |
| 6,282,440 | B1 * | 8/2001 | Brodnick et al. | 600/512 |
| 6,336,043 | B1 * | 1/2002 | Suzuki et al. | 600/409 |
| 6,526,313 | B2 * | 2/2003 | Sweeney et al. | 600/515 |

\* cited by examiner

*Primary Examiner*—Carl H Layno
*Assistant Examiner*—Natasha N Patel
(74) *Attorney, Agent, or Firm*—Andrus, Sceales, Starke & Sawall, LLP

(57) ABSTRACT

The two ECG channels are graphed as an X-Y pair where the X coordinate is the voltage in a first ECG channel and the Y coordinate is the voltage in a second ECG channel. Because neither of the coordinates is a measure of time, the system and method can collect ECG data over an extended period and collapse the data into a single display region.

25 Claims, 6 Drawing Sheets

VECTOR SUPERIMPOSITION AND GRAPHICAL DISPLAY OF PHYSIOLOGICAL DATA WITHOUT OR BEFORE ANALYSIS

FIELD OF INVENTION

The invention relates to the field of Graphical Display of Physiological Data. More particularly, the invention relates to the field of utilizing vector superimposition in electrocardiography (ECG) data displays.

BACKGROUND OF THE INVENTION

Electrocardiography (ECG) signals acquired over hours or days can represent a large volume of data, difficult to present for review in a succinct way. Analysis of the data (detection and classification of individual heart beats and rhythms) allows advanced displays that can compact the presentation while emphasizing clinically significant features. Analysis, however, can take some time, delaying display of the data. Often machine analysis has errors that can exaggerate unimportant features of the data or hide important features. Some devices, like simplistic ambulatory recorders or transmitters, may have no processing capability to do an analysis, and yet could benefit from a longer duration data display. In some cases, a good data display can provide a method to input guidance to an analysis algorithm from a human operator before analysis begins.

SUMMARY OF THE INVENTION

The present invention is a method and system for the graphical display of electrocardiography (ECG) physiological data using vector superimposition. The method and system graphs two channels of ECG physiological data over a period of time to include a plurality of heart beats. The two ECG channels are graphed as an X-Y pair where the X coordinate is the voltage in a first ECG channel and the Y coordinate is the voltage in a second ECG channel. Because neither of the coordinates is a measure of time, the system and method can collect ECG data over an extended period and collapse the data into a single display region.

DETAILED DESCRIPTION OF THE PRESENT INVENTION

Figure 1:
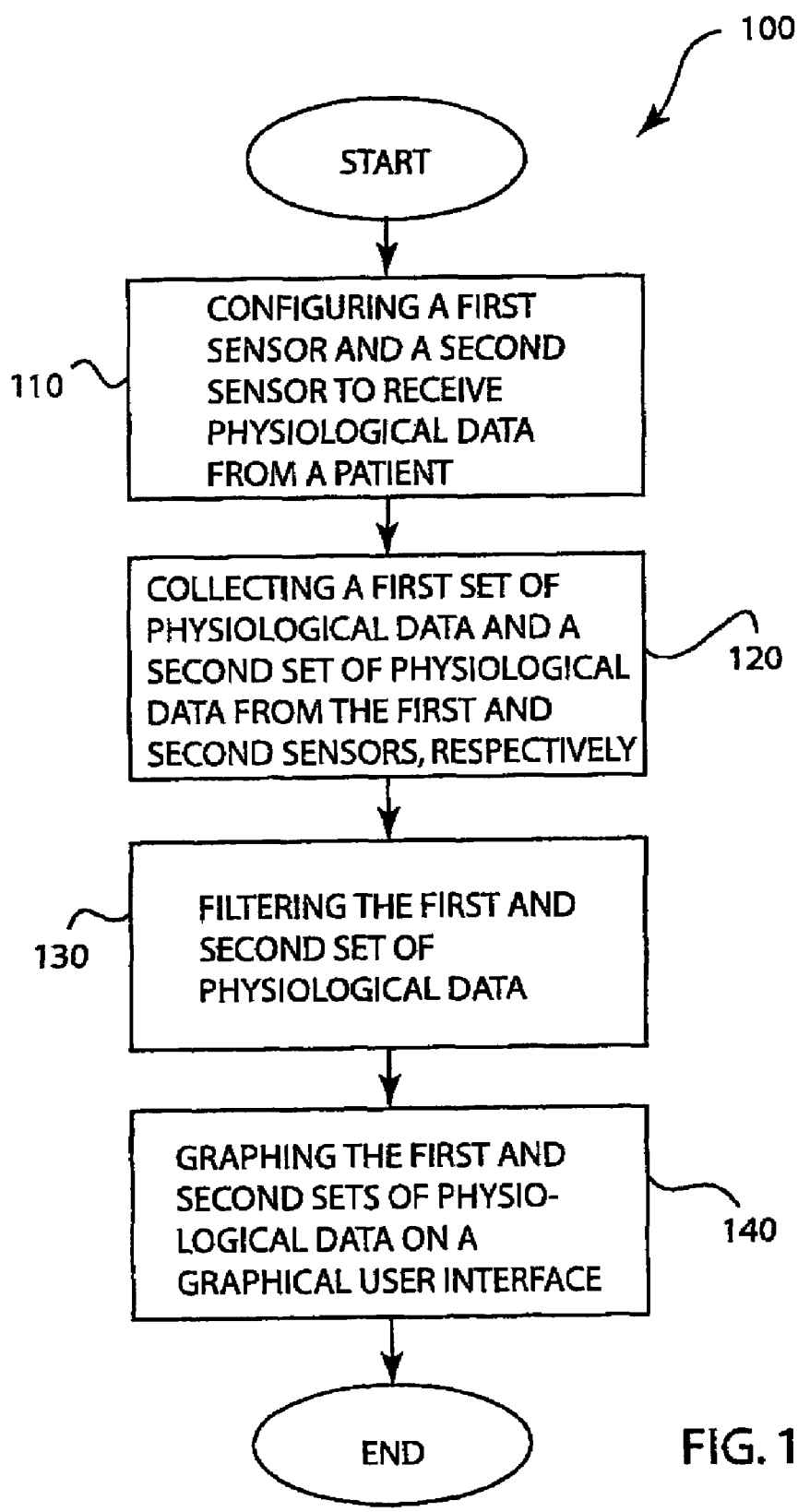
FIG. 1 is a flow chart illustrating a method according to an embodiment of the present invention.

A method of the preferred embodiment of the present invention is graphically represented in FIG. 1. In step 110 of the display method 100, a first sensor and a second sensor are configured to receive physiological data from a patient. The first sensor and the second sensor of step 110 may be part of an ECG sensor set as is known in the art. In such an embodiment, the physician is able to select which of the ECG sensors in the ECG sensor set are the first and second sensor of this display method 100. In step 120, a first set of physiological data and a second set of physiological data are collected from the first and second sensors, respectively. The first and second set of physiological data is collected over a predetermined time period and sent to a processor in step 130, where the processor filters the first and second set of physiological data. In step 140, the filtered physiological data is graphed on a graphical user interface, where the graphical user interface is implemented with a portable device or a workstation. Further in step 140, the sample point of the first and second sets of physiological data are graphed as an X-Y pair where the X coordinate is the voltage measured by the first sensor, and the Y coordinate is the voltage collected by the second sensor. It is also contemplated, that in step 140, the first and second sets of physiological data are graphed on an output device such as a printer or plotter, providing a user with a hard copy of the sets of physiological data. Such a device can be utilized in conjunction with, or in lieu of, a graphical user interface, and a hard copy can be produced before, during or after the sets of physiological data are graphed on the graphical user interface.

As described above, the two channel ECG data is graphed as a vector cardiograph loop over a period of time generally exceeding many heart beats. Preferably, signal data is high pass filtered with a corner frequency of between 0.5 and 1 Hz. Useful periods may be from six seconds (about 6 heart beats) to ten minutes (about 600 heart beats). Of course, larger or shorter periods may be used. Because each sample point is graphed as an X-Y pair where the X coordinate is the voltage in ECG channel 1 and the Y coordinate is the ECG voltage in channel 2, the graph will form a loop, naturally superimposing each heart beat on top of the previous heart beat. No analysis to detect and classify heart beats of the ECG is needed. Because neither axis is time, an extended period of time can be collapsed into a single square display region preferably about 2 mV on a side at a useful scale.

When a portable device such as a holter or telemetry monitor is used, one vector superimposition may be displayed within a 50 by 50 pixel space. Such a display could be updated every six seconds with a graph superimposing the last one minute of data. Viewing the display will give a good sense of signal quality as well as a record of recent ectopy in a small space with no processor analysis required. Of course, this is an example of how the present invention incorporates a portable device only, and should not limit such displays to particular inventory or particular sized displays.

When a workstation is used, a graphical record of 24 hours of two channel data could be presented on a single page as a 12 by 12 matrix of 10 minute loops. Again, this should not limit the size of the matrix, nor the type of workstation implemented. Periods of significant noise will be easily differentiated from periods of stable heart rhythms. Periods of arrhythmia can sometimes also be recognized, but at a contraction of 10 minutes per loop, arrhythmia is probably not reliably detected. If an interactive display is available, a clean and stable region of the ECG is easily found and can be identified to the machine as a region for algorithm learning. Almost as easily, it will be possible to identify regions of the data to mark as unreadable or as analyzable at some other more noise tolerant setting.

Figure 2:
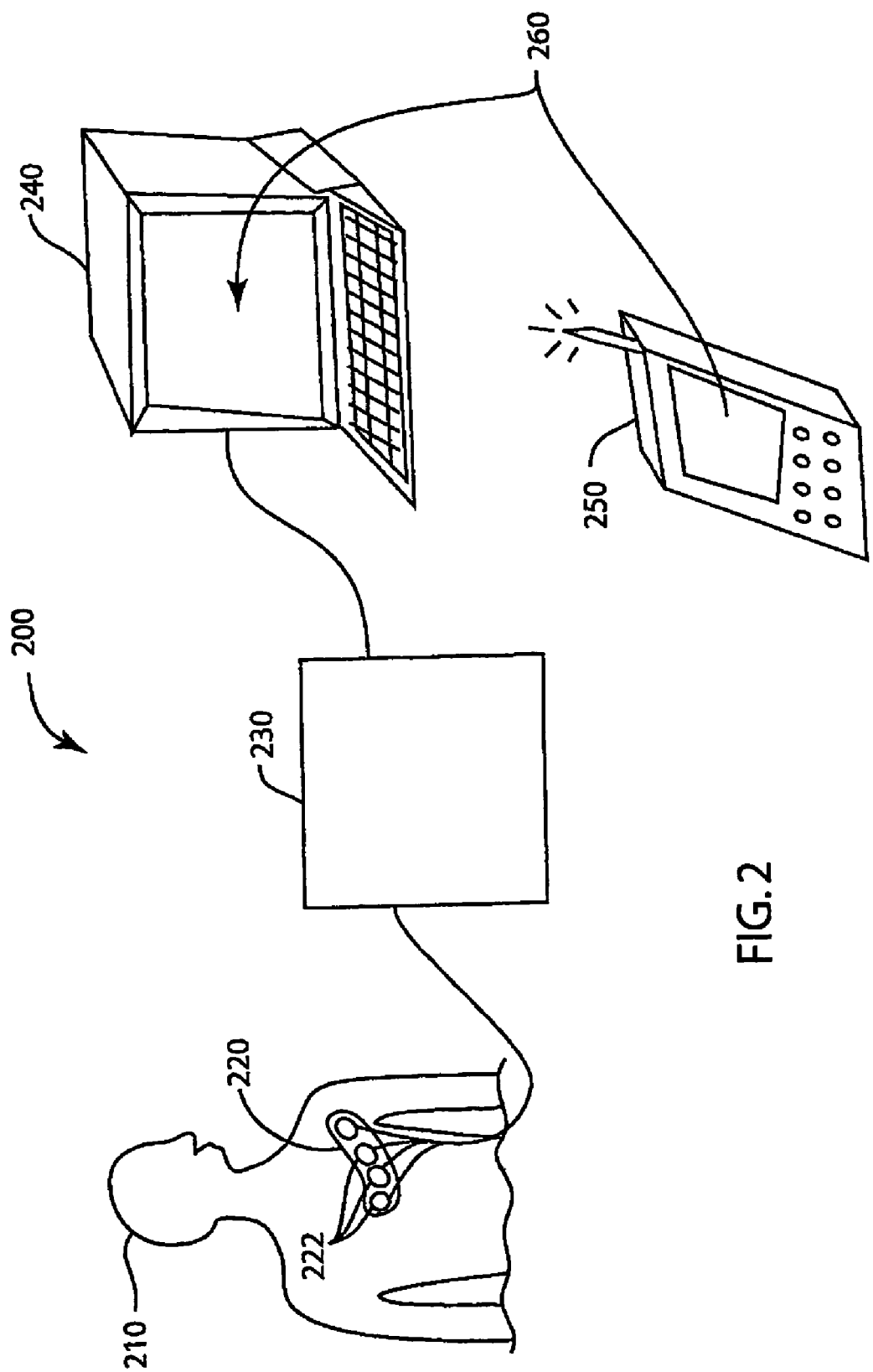
FIG. 2 is a graphical representation of a system according to an embodiment of the present invention.

A display system 200 of the present invention is depicted in FIG. 2. An ECG sensor set 220, having a set of ECG sensors 222 is attached to the patient 210. A user of the display system 200, such as a physician or technician, utilizes the workstation 240 or a portable device 250, having a graphical user interface 260, in order to select two of the ECG sensors 222 of the ECG sensor set 220. As described above, a printer or plotting output device can be utilized in conjunction with, or in lieu of, the graphical user interface 260 of the workstation 240 and/or portable device 250. The two ECG sensors 222 that are selected will collect two sets of physiological data from the patient to be displayed on the graphical user interface 260. It should be noted that while the user selects two of the ECG sensors 222 to use for collection of physiological data for display on the graphical user interface 260, all of the ECG sensors 222 of the ECG sensor set 220 are collecting physiological data from the patient. This allows the user to change either or both of the sensors for display on the graphical user interface 260, as the user chooses. The first and second set of physiological data that is collected from the ECG sensors 222 are sent to a processor 230 where they are filtered, before being transmitted to the device having the graphical user interface 260. The graphical user interface 260 may be implemented on a workstation 240, as described above, or a portable device 250, such as a holter monitor or a telemetry monitor. The graphical user interface 260 graphs the first set of physiological data as an X component and a second set of physiological data as a Y component, as will be described later in this specification.

Referring back to FIG. 2, a user interface implemented in the workstation 240 or portable device 250 that allows clicking on a loop to expand it into another matrix of much shorter time period loops would allow very quick access on the part of the operator to the most interesting ECG regions for precise marking of noise regions or arrhythmia regions. An exemplary configuration might be a 12 by 12 matrix of 10 minute loops at the top level going by one click to a 6 by 10 matrix of 10 second loops. Clicking on a second level loop would go directly to a 10 second strip display, preferably without replacing the 6 by 10 matrix on the same screen. The strip display would ideally fit on the screen with the 6 by 10 matrix. When more than two channels are available through the use of ECG sensor set 220 having multiple ECG sensors 222, user controls allow selection of which two channels are used in the loops.

The fact that the display system 200 is so useful without prior analysis or independent of analysis suggests it may be useful as a check of an automated analysis. Loops may be graphed of selected data. If after automated analysis loops were drawn of only those data segments thought to contain normal heart beats, many errors of beat detection and classification would be readily discerned.

Figure 3A:
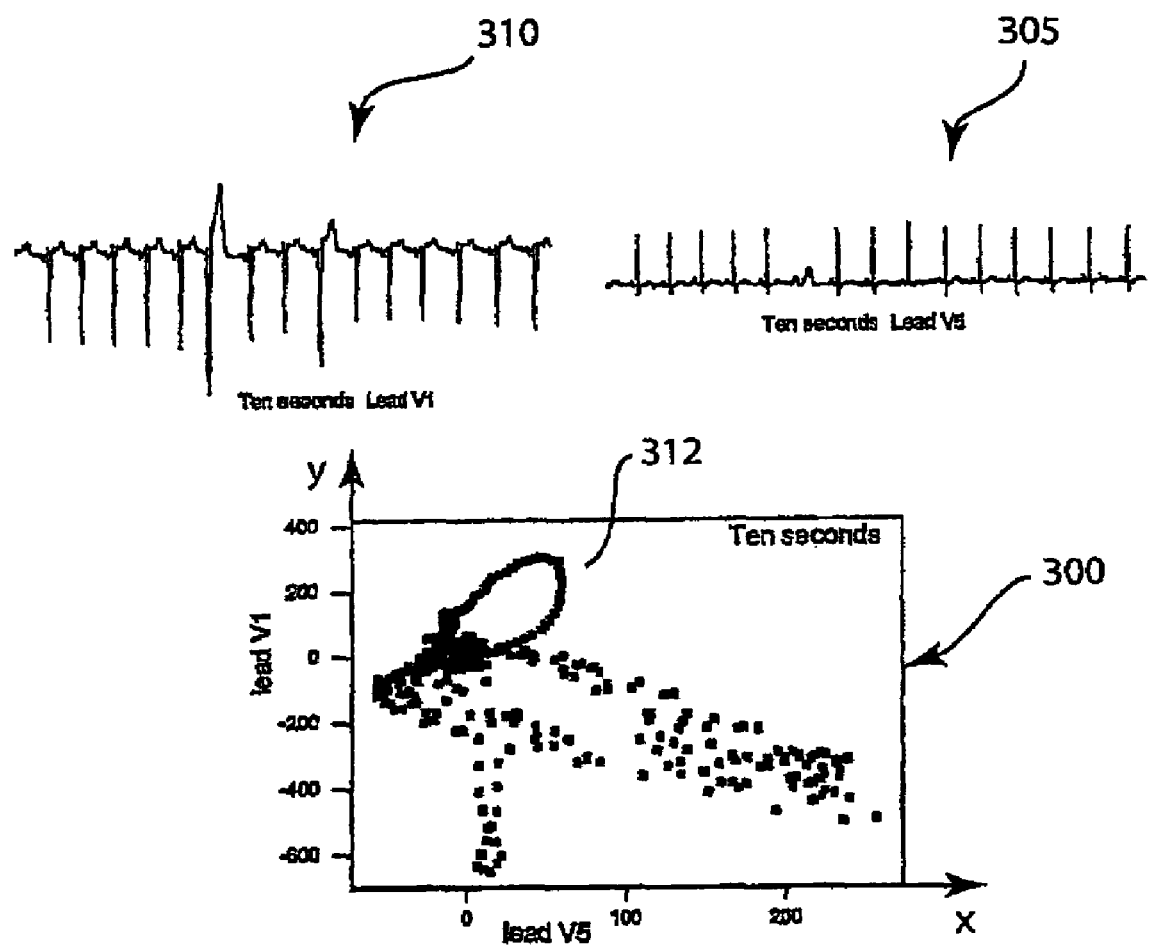
FIGS. 3A-3C are representations of exemplary graphical displays according to an embodiment of the present invention.

Referring to FIG. 3A, an exemplary ten second period of a first and second set of physiological data are depicted. The first set 305 and the second set 310 are configured here in FIG. 3A to show the voltage characteristics of both the first set 305 and the second set 310 over a ten second time period. This first set 305 and second set 310, depicted here in FIG. 3A, is exemplary of the filtered first and second set of physiological data. This first set 305 and second set 310 are displayed on the graphical user interface 300 by graphing the first set 305 on the X axis, and the second set 310 on the Y axis, thus producing the graphical image 312. As is evident by FIG. 3A, the graphical user interface 300 provides a much more compact and manageable representation of the physiological data collected by the sensors. This concept is further realized as the duration of the time period of the first set 305 and the second set 310 exceed ten seconds, and approach minutes, and even hours. While these graphical representations of the first set 305 and the second set 310 become long strings of data, the graphical user interface 300 remains the same size while the graphical image merely displays more data points. A single Premature Ventricular Contraction (PVC) causes the fat loop on top of the graphical image 312 and the projection straight downward. About 14 more normal R waves are superimposed to the right and slightly downward.

Figure 3B:
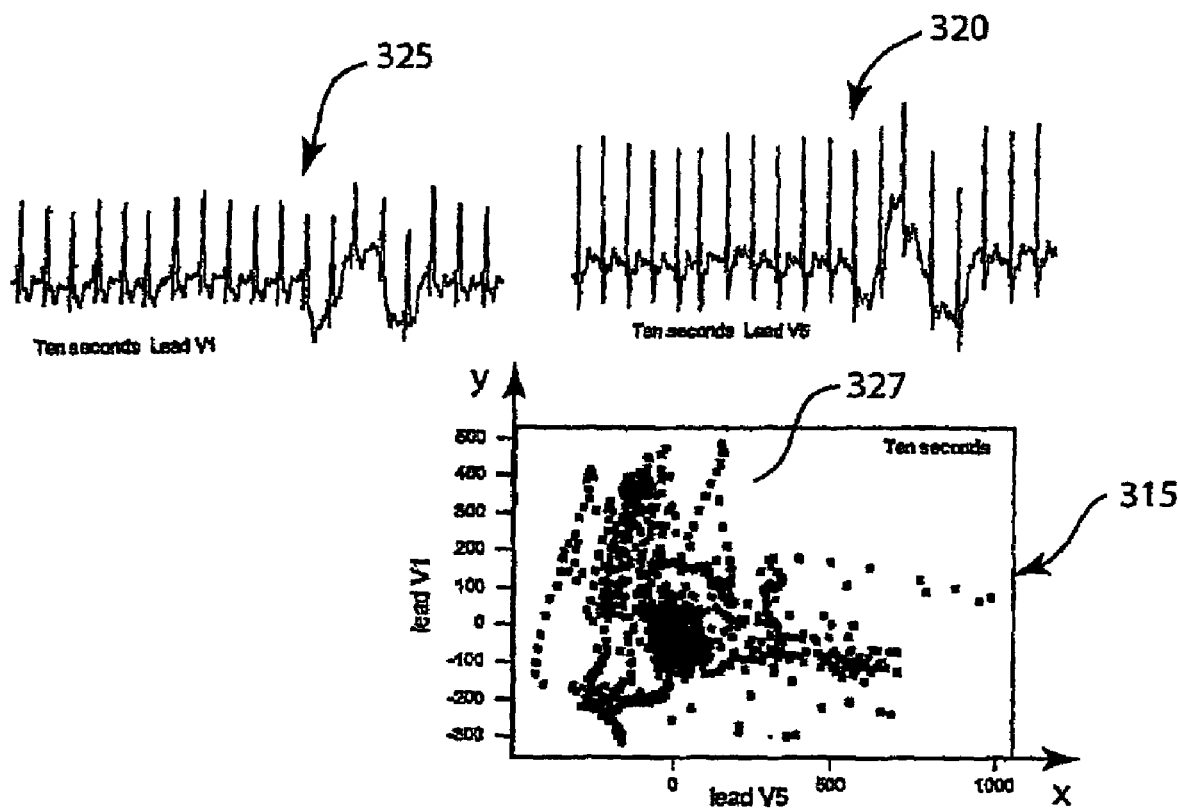

As in FIG. 3A, FIG. 3B illustrates a more noisy ten second period of physiological data. The vector superimposition is clearly more disorganized than the previous example. Here, the first set 320 and the second set 325 are again displayed in the graphical user interface 315, and plotted along the X and Y axis, respectively. It is clear that the graphical image 327 in FIG. 3B is quite different from the graphical image 312 of the 3A. Physicians will be able to identify and diagnose conditions based on the differences between graphical images.

Figure 3C:
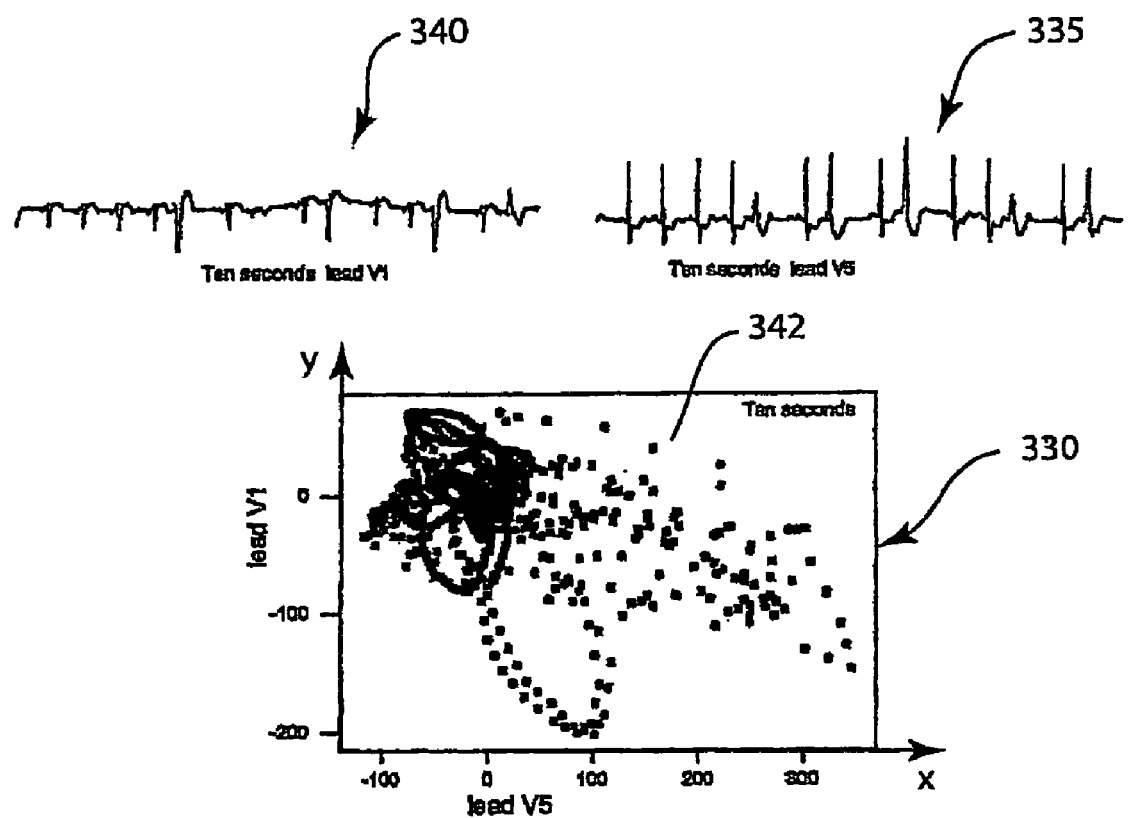

Again, FIG. 3C illustrates a relatively clean ten seconds of physiological data which also contains five ectopic heart beats. Again, the first set 335 and the second set 340 are displayed in the graphical user interface 330 by being graphed along the X and Y axis, thus creating the graphical image 342. With experience, regions of irregular heart rhythm like this may be discernable from regions of regular heart rhythm with noise, but what is most important is that with much less experience a technician will come to realize this region of ECG needs to be reviewed more closely. Providing the technician with a convenient and reliable way to quickly find the regions of ECG that need closer examination is an important benefit of this system.

Figure 4:
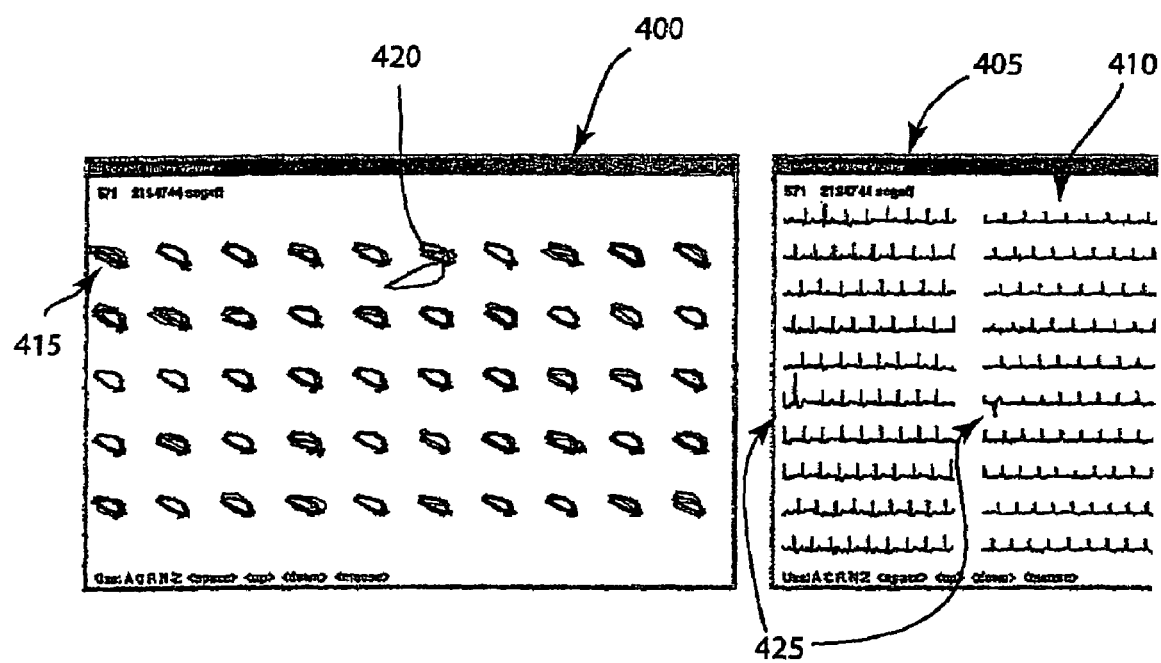
FIG. 4 is a representation of an exemplary graphical display according to an embodiment of the present invention.

Referring to FIG. 4, a graphical representation of the graphical user interface 400 showing a graphical image 415 representing the first set 405 and the second set 410 of physiological data over a longer period of time. Here, each graphical image 415 represents six seconds of physiological data 405, 410. Of course, FIG. 4 is exemplary and is shown only to provide an example of the obvious advantage of the present invention. It should be noted that the present invention may include any number of graphical images 415 over any preferred time period.

Five minutes of two channel physiological data 405, 410 is displayed in a 10 by 5 graphical user interface 400 matrix of six second vector superimposed graphical image 415 loops. An unusual extension from the sixth graphical image 420 loop in the top row motivated the user to display the one minute page of six second physiological data 405, 410. The PVC is visible in the sixth data strip 425 from top. An important observation here is that the graphical user interface 400 reviews five times as much data as the more conventional physiological data 405, 410 display. Graphical images 415 in the four rows below the top row would require additional pages of physiological data 405, 410 to review. Also, the scale of ECG voltage is twice as big (less miniaturized) in the GUI 400 at left.

A useful presentation of ECG and other physiological data can be made where automatic analysis is not available or not practical at a particular instant in time. A much longer duration of data can be presented, and at a larger scale, than normally in a display that charts against a time axis.

Having this display available the instant a holter test is acquired into a machine makes it practical for an operator to identify regions for algorithm learning and/or other regions for algorithm exclusion. This vector superimposition display may be perfect to guide an operator into choosing the best two channels to use in an automated ECG analysis. A much improved use may be made of a small LCD display on a portable acquisition system without a need for an analysis program in the portable unit.

In a conventional reviewing station, high speed review of two or more channels requires the technician to focus concentration on separate displays of superimposing waveforms, usually alternating attention from one channel to the other. A vector superimposition display combines the two channels into a single graph bringing double the information conveniently into the single focal point of the operator.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A method of displaying physiological data, the method comprising:

configuring a first sensor and a second sensor to receive physiological data from a patient;

collecting a plurality of first sets of physiological data from the first sensor and a plurality of second sets of physiological data from the second sensor, wherein each of the first sets of physiological data and the second set of physiological data are collected over a plurality of predetermined time periods;

graphing the plurality of first sets of physiological data and the plurality of second sets of physiological data on a graphical user interface, wherein the first set of physiological data is graphed as an X component and the second set of physiological data is graphed as a Y component, and further wherein a loop including the first and second sets of physiological data is graphed for each of the pre-determined time periods in a configurable matrix; and comparing the plurality of loops, and identifying a condition based on the comparison.

2. The method as claimed in claim 1, further comprising filtering the first and second set of physiological data after the first and second set of physiological data is collected.

3. The method as claimed in claim 1, wherein the predetermined time period is in a range from six seconds to ten minutes.

4. The method as claimed in claim 1, wherein the first and second set of physiological data is electrocardiography data.

5. The method as claimed in claim 4, wherein the first sensor and second sensor are part of an electrocardiography sensor set, further wherein the first and second sensor are any two sensors of the electrocardiography sensor set.

6. The method as claimed in claim 5, further comprising selecting the first sensor and the second sensor from the electrocardiography sensor set.

7. The method as claimed in claim 1, further comprising implementing the graphical user interface in a portable device.

8. The method as claimed in claim 7, wherein the portable device is a holter monitor.

9. The method as claimed in claim 7, wherein the portable device is a telemetry monitor.

10. The method as claimed in claim 1, further comprising implementing the graphical user interface in a patient monitor display.

11. The method as claimed in claim 1, further comprising implementing the graphical user interface in a workstation.

12. The method as claimed in claim 1, further comprising selectively adjusting the first and second set of physiological data after the graphing step, such that a portion of the first and second sets of physiological data are displayed.

13. The method as claimed in claim 1, further comprising graphing the first set of physiological data and the second set of physiological data with an output device over the predetermined time period.

14. A system for displaying physiological data, the system comprising:

a first sensor and a second sensor configured to collect physiological data from a patient, wherein a plurality of first sets of physiological data is collected from the first sensor and a plurality of second sets of physiological data is collected from the second sensor, further wherein the plurality of first sets of physiological data and the plurality of second sets of physiological data are collected over a plurality of predetermined time periods;

a processor configured to filter the plurality of first and second sets of physiological data; and a graphical user interface configured to graphically display the plurality of first sets of physiological data and the plurality of second sets of physiological data, wherein the first set of physiological data is graphed as an X component and the second set of physiological data is graphed as a Y component, and further wherein a loop including the first and second sets of physiological data is graphed for each of the pre-determined time periods in a configurable matrix.

15. The system as claimed in claim 14, wherein the predetermined time period is in a range from six seconds to ten minutes.

16. The system as claimed in claim 14, wherein the first and second set of physiological data is electrocardiography data.

17. The system as claimed in claim 16, wherein the first sensor and second sensor are part of an electrocardiography sensor set, further wherein the first and second sensor are any two sensors of the electrocardiography sensor set.

18. The system as claimed in claim 14, wherein the graphical user interface is implemented in a portable device.

19. The system as claimed in claim 18, wherein the portable device is a holter monitor.

20. The system as claimed in claim 18, wherein the portable device is a telemetry monitor.

21. The system as claimed in claim 14, wherein the graphical user interface is implemented in a patient monitor display.

22. The system as claimed in claim 14, wherein the graphical user interface is implemented in a workstation.

23. The system as claimed in claim 14, wherein the first and second set of physiological data are selectively adjusted after the graphing step, such that a portion of the first and second sets of physiological data are displayed.

24. The system as claimed in claim 14, further comprising an output device configured to graph the first set of physiological data and the second set of physiological data over a predetermined time period.

25. A method of vector superimposition and graphical display of electrocardiography data, the method comprising:

collecting a plurality of first sets of physiological data from a patient with a first sensor and a plurality of second sets of physiological data from the patient with a second sensor, wherein the plurality of first and second sets of physiological data are collected over a plurality of predetermined time periods; and displaying the plurality of first and second sets of physiological data on a graphical user interface, wherein the graphical user interface is configured such that the first set of physiological data represents an X component and the second set of physiological data represents a Y component, and further wherein a loop including the first and second sets of physiological data is graphed for each of the pre-determined time periods in a configurable matrix.

* * * * *